United States Patent
Soultanidis et al.

(10) Patent No.: US 10,647,633 B2
(45) Date of Patent: May 12, 2020

(54) CATALYST AND PROCESS FOR THE PRODUCTION OF PARA-XYLENE

(71) Applicant: ExxonMobil Chemical Patents Inc., Baytown, TX (US)

(72) Inventors: Nikolaos Soultanidis, Houston, TX (US); Todd E. Detjen, Houston, TX (US); Scott J. Weigel, Allentown, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/075,727

(22) PCT Filed: Jan. 27, 2017

(86) PCT No.: PCT/US2017/015212
§ 371 (c)(1),
(2) Date: Aug. 6, 2018

(87) PCT Pub. No.: WO2017/164981
PCT Pub. Date: Sep. 28, 2017

(65) Prior Publication Data
US 2019/0039968 A1    Feb. 7, 2019

Related U.S. Application Data

(60) Provisional application No. 62/313,313, filed on Mar. 25, 2016.

(30) Foreign Application Priority Data

May 20, 2016    (EP) ..................... 16170703

(51) Int. Cl.
*C07C 2/86*    (2006.01)
*B01J 29/42*    (2006.01)
(Continued)

(52) U.S. Cl.
CPC ............. *C07C 2/864* (2013.01); *B01J 29/405* (2013.01); *B01J 29/42* (2013.01); *B01J 29/44* (2013.01);
(Continued)

(58) Field of Classification Search
None
See application file for complete search history.

(56) References Cited

U.S. PATENT DOCUMENTS

| | | | |
|---|---|---|---|
| 4,002,698 | A | 1/1977 | Kaeding |
| 4,356,338 | A | 10/1982 | Young |

(Continued)

FOREIGN PATENT DOCUMENTS

| | | |
|---|---|---|
| FR | 2 285 176 A | 4/1976 |
| WO | 96/16004 A | 5/1996 |

(Continued)

OTHER PUBLICATIONS

Bouizi et al.; "Factors Controlling the Formation of Core-Shell Zeolite-Zeolite Composites", Chem. Mater. 2006, 18, 4959-4966. (Year: 2006).*

(Continued)

*Primary Examiner* — Ali Z Fadhel

(57) ABSTRACT

A fluidized bed process for producing para-xylene via toluene and/or benzene methylation with methanol using a dual function catalyst system. A first catalyst accomplishes the toluene and/or benzene methylation and a second catalyst converts the by-products of the methylation reaction or unconverted methylating agent, improves the yields of the desired products, or a combination thereof. The inclusion of the second catalyst can suppress the $C_1$-$C_5$ non-aromatic fraction by over 50% and significantly enhance the formation of aromatics.

18 Claims, 3 Drawing Sheets

(51) Int. Cl.
*B01J 29/46* (2006.01)
*B01J 29/40* (2006.01)
*B01J 37/28* (2006.01)
*C07C 15/067* (2006.01)
*B01J 29/44* (2006.01)
*B01J 29/80* (2006.01)
*B01J 37/00* (2006.01)
*B01J 35/00* (2006.01)

(52) U.S. Cl.
CPC ............... *B01J 29/46* (2013.01); *B01J 29/80* (2013.01); *B01J 37/0045* (2013.01); *B01J 37/28* (2013.01); *C07C 2/865* (2013.01); *C07C 15/067* (2013.01); *B01J 35/008* (2013.01); *B01J 2229/186* (2013.01); *B01J 2229/36* (2013.01); *B01J 2229/42* (2013.01); *B01J 2229/62* (2013.01); *C07C 2529/40* (2013.01); *C07C 2529/80* (2013.01); *Y02P 20/52* (2015.11)

(56) References Cited

U.S. PATENT DOCUMENTS

| | | | |
|---|---|---|---|
| 4,423,266 A | 12/1983 | Young | |
| 5,675,047 A | 10/1997 | Beck et al. | |
| 5,804,690 A | 9/1998 | Chang et al. | |
| 5,939,597 A | 8/1999 | Dessau et al. | |
| 6,028,238 A | 2/2000 | Beck et al. | |
| 6,046,372 A | 4/2000 | Brown et al. | |
| 6,048,816 A | 4/2000 | Brown et al. | |
| 6,111,157 A * | 8/2000 | Hendriksen | B01J 29/80 502/67 |
| 6,156,949 A | 12/2000 | Brown et al. | |
| 6,423,879 B1 | 7/2002 | Brown et al. | |
| 6,504,072 B1 | 1/2003 | Brown et al. | |
| 6,506,954 B1 | 1/2003 | Brown et al. | |
| 6,538,167 B1 | 3/2003 | Brown et al. | |
| 6,642,426 B1 | 11/2003 | Johnson et al. | |
| 7,396,967 B2 | 7/2008 | Iaccino et al. | |
| 7,453,018 B2 | 11/2008 | Dakka et al. | |
| 7,799,962 B2 | 9/2010 | Dakka et al. | |
| 9,079,163 B2 | 7/2015 | Nakaoka et al. | |
| 9,095,831 B2 | 8/2015 | Han et al. | |
| 9,440,893 B2 | 9/2016 | Helton et al. | |
| 9,738,573 B2 | 8/2017 | Molinier et al. | |
| 2006/0011514 A1 | 1/2006 | Van Den Berge et al. | |
| 2012/0004487 A1 | 1/2012 | Igarashi et al. | |
| 2013/0072736 A1* | 3/2013 | Nakaoka | B01J 29/40 585/467 |
| 2017/0088488 A1 | 3/2017 | Shekhar et al. | |

FOREIGN PATENT DOCUMENTS

| | | |
|---|---|---|
| WO | 97/45387 A | 12/1997 |
| WO | 98/14415 A | 4/1998 |
| WO | 2016/003612 A | 1/2016 |
| WO | 2016/003613 A | 1/2016 |
| WO | 2016/032639 A | 3/2016 |

OTHER PUBLICATIONS

Ji, Y.-J. et al., "Core/shell-structured Al-MWW@B-MWW zeolites for shape-selective toluene disproportionation to para-xylene" Journal of Catalysis, vol. 283, pp. 168-177, 2011.

Zhang, J., et al., "Influence of Catalyst Acidity on Dealkylation, Isomerization and Alkylation in MTA Process", Acta Phys.-Chim Sin., vol. 29, No. 6, pp. 1281-1288, 2013.

Zhang, J., "Increasing Para-xylene Selectivity in Making Aromatics from Methanol with a Surface-Modified Zn/P/ZSM-5 Catalyst", ACS Catalysis, vol. 5, No. 5, pp. 2982-2988, 2015.

* cited by examiner

CATALYST AND PROCESS FOR THE PRODUCTION OF PARA-XYLENE

CROSS-REFERENCE OF RELATED APPLICATIONS

This application is a National Phase Application claiming priority to PCT Application Serial No. PCT/US2017/015212 filed Jan. 27, 2017, which claims priority to and the benefit of U.S. Provisional Application No. 62/313,313 filed Mar. 25, 2016, and EP Application No. 16170703.9, filed May 20, 2016, the disclosure of each being incorporated herein by reference in their entireties for all purposes.

FIELD

This disclosure relates to a catalyst and process for producing para-xylene by the alkylation of benzene and/or toluene with methanol.

BACKGROUND

Of the xylene isomers, para-xylene is of particular value since it is useful in the manufacture of terephthalic acid which is an intermediate in the manufacture of synthetic fibers. Today, para-xylene is commercially produced by hydrotreating of naphtha (catalytic reforming), steam cracking of naphtha or gas oil, and toluene disproportionation.

One problem with most existing processes for producing xylenes is that they produce a thermodynamic equilibrium mixture of ortho (o)-, meta (m)- and para (p)-xylenes, in which the para-xylene concentration is typically only about 24 wt %. Thus, separation of para-xylene from such mixtures typically requires superfractionation and multistage refrigeration steps. Such processes involve high operational costs and result in only limited yields. There is therefore a continuing need to provide processes for producing xylenes which are highly selective for para-isomers.

It is well-known to manufacture xylenes by the alkylation of toluene and/or benzene with methanol, and, in particular, to selectively make para-xylene (PX) product using zeolite catalyst. See, for instance, U.S. Pat. Nos. 4,002,698; 4,356,338; 4,423,266; 5,675,047; 5,804,690; 5,939,597; 6,028,238; 6,046,372; 6,048,816; 6,156,949; 6,423,879; 6,504,072; 6,506,954; 6,538,167; and 6,642,426. The terms "para-xylene selectivity", "para-selective", and the like, means that para-xylene is produced in amounts greater than is present in a mixture of xylene isomers at thermodynamic equilibrium, which at ordinary processing temperatures is about 24 mol %. Para-xylene selectivity is highly sought after because of the economic importance of para-xylene relative to meta- and ortho-xylene. Although each of the xylene isomers have important and well-known end uses, para-xylene is currently the most economically valuable.

In the process, typically toluene and/or benzene are alkylated with methanol, in the presence of a suitable catalyst, to form xylenes in a reactor in a system illustrated schematically in FIG. 1, wherein a feed comprising reactants enter fluid bed reactor 11 via conduit 1 and effluent comprising product exits through conduit 5, and the catalyst circulates between fluid bed reactor 11, apparatus 12, which strips fluid from the catalyst, and catalyst regenerator 13, via conduits 2, 3, and 4, respectively. Water is typically co-fed with toluene and methanol to minimize toluene coking in the feed lines and methanol self-decomposition. Other side reactions include the formation of light olefins, light paraffins, as reactions that convert para-xylenes to other xylene isomers or heavier aromatics.

Although toluene methylation, and particularly the para-selective toluene methylation process of U.S. Pat. No. 6,504,072, provides an attractive route to para-xylene, the process inevitably produces significant quantities of $C_1$-$C_5$ non-aromatics. Therefore, it is desirable to suppress the formation of $C_1$-$C_5$ non-aromatics and produce more aromatics in the toluene methylation reaction.

SUMMARY

Some embodiments disclosed herein provide a process and dual-function catalyst system for the methylation of toluene and/or benzene in a fluidized bed reactor. Because of the nature of the fluidized bed reactor, the dual-function catalyst system is preferably a core-shell catalyst, meaning a catalyst that contains one zeolite structure, i.e., the shell, that performs one type of chemical reactions, with a similar or different zeolite structure, i.e., the core, that performs or promotes different reactions. In one embodiment, the core-shell catalyst comprises shell zeolite crystals to accomplish the toluene methylation reaction and core zeolite crystals to either further convert the olefins and paraffins formed as byproducts in the toluene methylation reaction or unconverted methylating agent, improve the yields of desired products such as aromatics, or both. The inclusion of the second catalyst can suppress the $C_1$-$C_5$ non-aromatic fraction by over 50% and significantly enhance the formation of aromatics.

The process includes providing, in a fluidized bed reactor, a catalyst comprising core crystals of a first medium-pore size aluminosilicate zeolite and a discontinuous layer of shell crystals of a second medium-pore size aluminosilicate zeolite covering at least a portion of the external surface of the core crystals. The shell crystals may be the same as or different from the core crystals. In one embodiment, the shell crystals comprise ZSM-5 having a silica/alumina molar ratio of at least 200, as measured prior to any steaming of the catalyst, and phosphorus or a compound thereof, wherein the catalyst has been steamed at a temperature of at least 900° C., wherein said steamed catalyst has a Diffusion Parameter for 2,2 dimethylbutane of about 0.1-15 $sec^{-1}$ when measured at a temperature of 120° C. and a 2,2 dimethylbutane pressure of 60 torr (8 kPa). The core crystals may also be ZSM-5, either with a higher activity and/or higher para-xylene selectivity than the shell crystals or with a metal incorporated therein to further convert olefins and paraffins. The core-shell catalyst alkylates $C_{6+}$ aromatic hydrocarbons with an alkylating agent selected from methanol, dimethyl ether, and mixtures thereof, in the presence of the shell crystals under conditions including a temperature of at least 400° C., and converts olefins and/or paraffins formed, unconverted alkylating agent, and unconverted $C_{6+}$ aromatic hydrocarbons to para-xylene in the presence of the core crystals.

Some embodiments disclosed herein also include a catalyst system that comprises core crystals of a first medium-pore size aluminosilicate zeolite and a discontinuous layer of shell crystals of a second medium-pore size aluminosilicate zeolite, which may be the same as or different from the core crystals, covering at least a portion of the external surface of the core crystals. The shell crystals are effective to accomplish toluene methylation and the core crystals are effective to convert olefin and/or paraffin by-products formed by the toluene methylation reaction and/or improve the yield of aromatics.

These and other objects, features, and advantages will become apparent in the following detailed description, drawings, specific embodiments, experiments, and accompanying claims.

DETAILED DESCRIPTION OF THE EMBODIMENTS

At least some embodiments disclosed herein include a fluidized bed process for producing para-xylene via toluene and/or benzene methylation with methanol using a dual function catalyst system. A first catalyst accomplishes the toluene and/or benzene methylation and a second catalyst converts the by-products of the methylation reaction or unconverted methylating agent, improves the yields of the desired products, or a combination thereof. The inclusion of the second catalyst can suppress the $C_1$-$C_5$ non-aromatic fraction by over 50% and significantly enhance the formation of aromatics.

For the purposes of this description and claims, reference to a group number for an element corresponds to the International Union of Pure and Applied Chemistry (IUPAC) Periodic Table version dated 1 May 2013.

As used herein, "toluene methylation" may also include benzene methylation.

The alkylation process employed herein can use any aromatic feedstock comprising toluene and/or benzene, although in general it is preferred that the aromatic feed contains at least 90 weight % (wt %), especially at least 99 wt %, of benzene, toluene or a mixture thereof. An aromatic feed containing at least 99 wt % toluene is particularly desirable in at least some embodiments. Similarly, although the composition of the methanol-containing feed is not critical, it is generally desirable to employ feeds containing at least 90 wt %, especially at least 99 wt %, of methanol.

The dual function catalyst system employed in the alkylation process is preferably a "core-shell" catalyst or coated catalyst. Using a dual function catalyst system in a fluidized bed reactor poses unique challenges since stacking the two catalysts is not an option. One possible solution is to include both catalysts in the reactor but there is no control of the reaction mechanisms in this scenario because all of the reactions will occur at the same time. Another possible solution is to utilize two reactors in sequence, but this is not preferred for capital reasons. A core-shell catalyst allows the use of a single reactor and management of the two reaction mechanisms. As used herein, a core-shell catalyst or coated catalyst means a catalyst that contains one zeolite structure, i.e., the shell, that performs one type of chemical reactions, with a similar or different zeolite structure, i.e., the core, that performs or promotes different reactions. One or both of the zeolite structures may also contain a metal. The terms core-shell catalyst and coated catalyst may be used interchangeably herein. Examples of coated catalysts are found in U.S. Pat. No. 7,335,295, which is incorporated herein by reference.

Figure 1:
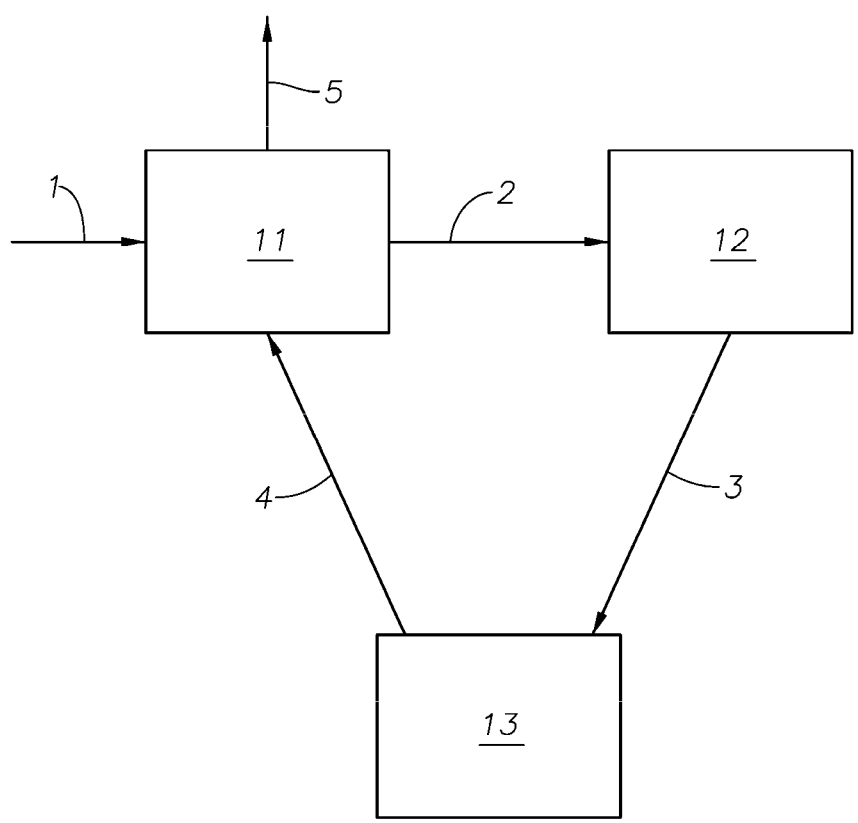
FIG. 1 is a schematic of a reactor system including reactor and regenerator and some associated auxiliary devices and transfer piping per se known in the art.
Figure 2:
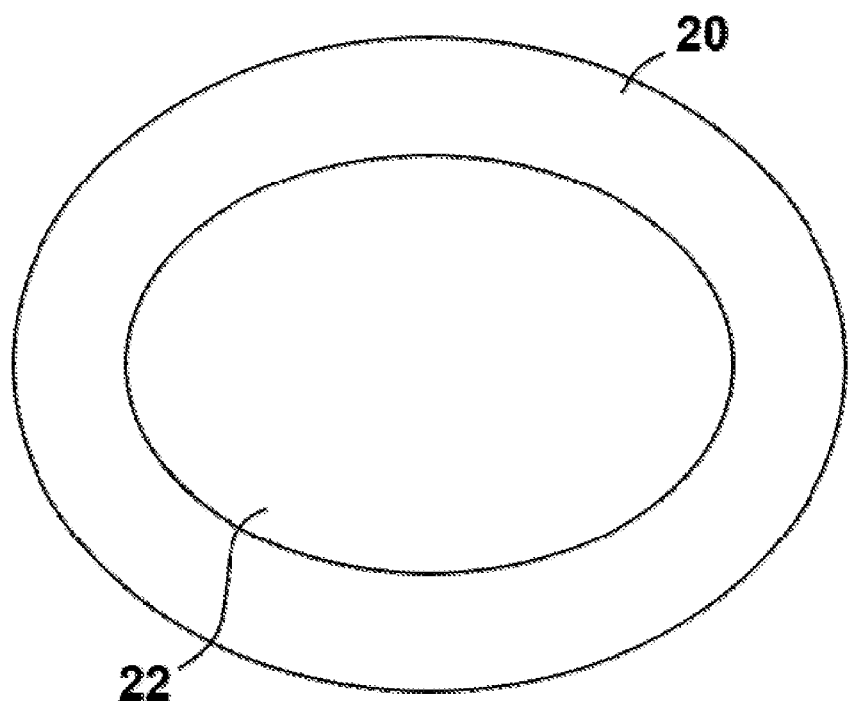
FIG. 2 is a schematic view of a core-shell catalyst in accordance with at least some embodiments disclosed herein.

Referring now to FIG. 2, the core-shell catalyst of embodiments disclosed herein contains a coating of second crystals 20, known herein as the shell crystals, of a second zeolite covering at least a portion of the external surface of the first crystals 22, known herein as the core crystals. The shell crystals 20 can grow together and form an overgrowth over the core crystals 22. By coating the core crystals 22 with the shell crystals 20, the accessibility of reactants and products to the external surface acid sites of the core zeolite 22 is reduced. The term "coating" as used in the specification and claims, means that a discontinuous layer of second or shell zeolite crystals (e.g., second crystals 20) is formed, such as by being deposited or grown on, covering at least a portion of the external surface of the first or core zeolite crystals (e.g., first crystals 22) such that the shell zeolite crystals are non-continuous with the core crystals, i.e., the crystalline framework of the shell zeolite crystals is not part of or a continuation of the framework of the core zeolite. Hence, the layer deposited on the core zeolite crystals 22 is not isocrystalline with the core crystals 20. It should be appreciated that the representation of the crystals 20, 22 in FIG. 2 is schematic in nature, and should not be interpreted as particularly defining the specific physical shape of embodiments of the core-shell catalyst.

Preferably, the shell crystals 20 will cover at least 20 percent (i.e., 20%) of the outer surface of the core crystals 22 and more preferably will cover at least 75 percent (i.e., 75%) of the external surface of the core crystals. While FIG. 2 shows the shell crystals 20 covering substantially all of the outer surface of the core crystals 22, it should be appreciated that such total coverage is not required and that in at least some embodiments, the shell crystals 20 may cover less than all of the outer surface of the core crystals 22. The coating (e.g., of shell crystals 20) will usually be non-uniform and may adhere to the surface of the core crystals 22. Another way to describe the coverage of the shell crystals 20 is the ratio of shell crystals 20 to core crystals 22. In some embodiments, the ratio of shell crystals 20 to core crystals 22 is 20:1, or 10:1, or 8:1, or 5:1, or 2:1.

In one embodiment, the core-shell catalyst comprises shell zeolite crystals 20 to accomplish the toluene methylation reaction and core zeolite crystals 22 to either further convert the olefins and paraffins formed as byproducts in the toluene methylation reaction, improve the yields of desired products such as aromatics, or both.

The shell crystals 20 of the core-shell catalyst comprise a medium-pore size aluminosilicate zeolite, preferably steamed, modified with phosphorus, and in its proton form, such as that described in U.S. Pat. No. 9,012,711, which is incorporated herein by reference. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, ZSM-48, and MOR, with ZSM-5 and ZSM-11 being particularly preferred. Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described U.S. Pat. No. 4,076,842. Zeolite ZSM-35 and the conventional preparation thereof are described in U.S. Pat. No. 4,016,245. ZSM-48 and the conventional preparation thereof is taught by U.S. Pat. No. 4,375,573. The entire disclosures of these U.S. patents are incorporated herein by reference.

In at least some embodiments, the medium pore zeolite is ZSM-5. The ZSM-5 employed in the present process is typically an aluminosilicate or silicate having a silica ($SiO_2$) to alumina ($Al_2O_3$) molar ratio of at least 200, preferably 350, and more preferably 450, as measured prior to any steaming of the catalyst to adjust its diffusivity. After steaming (described below), the silica ($SiO_2$) to alumina ($Al_2O_3$) molar ratio may be at least 900.

The shell zeolite crystals 20 employed in the present process are preferably steamed such that the steamed catalyst has a Diffusion Parameter for 2,2 dimethylbutane of about 0.1-15 $sec^{-1}$ when measured at a temperature of 120° C. and a 2,2 dimethylbutane pressure of 60 torr (8 kPa). As used herein, the Diffusion Parameter of a particular porous crystalline material is defined as $D/r^2 \times 10^6$, wherein D is the diffusion coefficient ($cm^2$/sec) and r is the crystal radius (cm). The diffusion parameter can be derived from sorption measurements provided the assumption is made that the plane sheet model describes the diffusion process. Thus for a given sorbate loading Q, the value $Q/Q_{eq}$, where $Q_{eq}$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The medium pore zeolites described above are preferred for the present process since the size and shape of their pores favor the production of p-xylene over the other xylene isomers. However, conventional forms of these zeolites have Diffusion Parameter values in excess of the 0.1-15 $sec^{-1}$ range desired for the present process. Nevertheless, the required diffusivity can be achieved by severely steaming the zeolite so as to effect a controlled reduction in the micropore volume of the catalyst to not less than 50%, and preferably 50-90%, of that of the unsteamed catalyst. Reduction in micropore volume is monitored by measuring the n-hexane adsorption capacity of the zeolite, before and after steaming, at 90° C. and 75 torr n-hexane pressure.

Steaming to achieve the desired diffusivity and reduction in the micropore volume of the porous crystalline material can be effected by heating the material in the presence of steam at a temperature of at least about 900° C., preferably about 950 to about 1075° C., and most preferably about 1000 to about 1050° C., and for time period of from about 10 minutes to about 10 hours, preferably from 30 minutes to 5 hours, such as 30 minutes to 2 hours. Other preferred temperature and temperature ranges include any of the lower temperatures and/or times listed in this paragraph to any of the higher temperatures and/or times listed herein, e.g., from about 900 to 1050° C. for about 10 minutes to 2 hours, and so on.

To effect the desired controlled reduction in diffusivity and micropore volume, it may be desirable to combine the porous crystalline material, prior to steaming, with at least one oxide modifier, preferably selected from oxides of the elements of Groups IIA, IIIA, IIIB, IVA, VA, VB and VIA of the Periodic Table (IUPAC version). Conveniently, said at least one oxide modifier is selected from oxides of boron, magnesium, calcium, lanthanum and preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt %, such as between about 0.1 and about 10 wt %, based on the weight of the final catalyst.

Where the modifier includes phosphorus, incorporation of phosphorus modifier in the catalyst is conveniently achieved by the methods described in U.S. Pat. Nos. 4,356,338, 5,110,776, 5,231,064 and 5,348,643, the entire disclosures of which are incorporated herein by reference. Treatment with phosphorus-containing compounds can readily be accomplished by contacting the ZSM-5, either alone or in combination with a binder material, with a solution of an appropriate phosphorus compound, followed by drying and calcining to convert the phosphorus to its oxide form. Contact with the phosphorus-containing compound is generally conducted at a temperature between about 25° C. and about 125° C. for a time between about 15 minutes and about 20 hours. The concentration of the phosphorus in the contact mixture may be between about 0.01 and about 30 wt %.

After preparation of the phosphorus-containing compound, the catalyst may be dried and calcined to convert the phosphorus to an oxide form. Calcination can be carried out in an inert atmosphere or in the presence of oxygen, for example, in air at a temperature between about 150 to 850° C., such as from 300 to 650° C., or about 540 to 810° C., for at least 30 minutes (mins), such as from 45 to 90 mins or from 30 to 60 mins.

Representative phosphorus-containing compounds which may be used to incorporate a phosphorus oxide modifier into the catalyst have been previously disclosed in U.S. Pat. No. 6,504,072.

The phosphorus oxide modifier is generally present in the catalyst in an amount such that the catalyst contains from 1 to 10 wt %, for example from 2 to less than 8 wt %, such as from 2 to 6 wt %, of phosphorus, based on elemental phosphorus.

In an embodiment, the phosphorus source, such as phosphoric acid, is added to a slurry of ZSM-5 in deionized water. Then clay, for example a kaolin clay, such as Thiele RC-32, is then added to the slurry of ZSM-5 and phosphorus compound. The spray dried product from this step is then calcined, preferably in air and at a nominal temperature of between about 540-810° C., prior to steaming.

The core crystals 22 of the core-shell catalyst are an aluminosilicate zeolite that can further convert reactants that were not converted by the shell crystals, aromatize the olefins and paraffins formed as byproducts in the toluene methylation reaction, thereby improving the yield of desired aromatics.

In one embodiment, the core crystals 22 comprise a medium pore size aluminosilicate zeolite, such as those described above. In a preferred embodiment, the medium-pore size zeolite is ZSM-5, which may be in the proton form (HZSM-5), having a silica ($SiO_2$) to alumina ($Al_2O_3$) molar ratio of about 10 to 800, preferably about 10 to 400, more preferably about 20 to 200, and most preferably about 20 to 100, as measured prior to any steaming of the catalyst. The core crystals 22 of the core-shell catalyst may also include at least one element selected from Groups 6-14 of the Periodic Table. Typically, the total weight of the Group 6-14 elements is at least 0.01 wt. % and less than about 20.0 wt. %, preferably about 0.01 to 10.0 wt. %, more preferably about 0.01 to 2.0 wt. %, and most preferably about 0.01 to 1.0 wt. %, the weight percent excluding any binder that may be used and based on the core mass basis, not on the total core/shell mass. Of course, the total weight of the Group 6-14 elements shall not include amounts attributable to the molecular sieve itself or any binder that is used. Preferably, the Group 6-14 element is selected from Zn, Ga, Cu, Re, Mo, W, La, Fe, Ag, Pt, or Pd. More preferably, the Group 6-14 element is Ga or Zn. The inclusion of a Group 6-14 metal aids in the conversion of the olefins and paraffins by-products to more aromatics, thereby improving the yield of desired aromatic products.

In another embodiment, the core crystals 22 comprise a medium pore zeolite, such as ZSM-5, as described above in relation to the shell crystals, but with a higher activity, a higher para-xylene selectivity, or a combination thereof. To achieve the higher activity level, the zeolite has a lower silica ($SiO_2$) to alumina ($Al_2O_3$) molar ratio. In one embodiment where the shell crystals have a silica ($SiO_2$) to alumina ($Al_2O_3$) molar ratio of greater than 450 prior to steaming, the core zeolite has a silica ($SiO_2$) to alumina ($Al_2O_3$) molar ratio of less than 450, prior to any steaming, or silica ($SiO_2$) to alumina ($Al_2O_3$) molar ratio of less than 900 after any steaming, increased acid sites, and increased strength of acid sites. This higher activity catalyst consumes the olefin by-products of the toluene methylation reaction and makes additional aromatics and light paraffins by an aromatization reaction. Alternatively, or in addition to the higher activity level, the zeolite may be more selective to para-xylene. This may be achieved by steaming the zeolite.

In yet another embodiment, the core crystals 22 comprise a different zeolite than ZSM-5. The zeolite may be any zeolite with a three-dimensional structure, such as ZSM-11, ZSM-12, ZSM-22, ZSM-23, ZSM-35, ZSM-48, or those in the SAPO family. The zeolite may be chosen based on the desired reaction to conduct within the core and/or the desired characteristics.

The core zeolite crystals 22 employed in the present process may be steamed to achieve the desired diffusivity and reduction in the micropore volume of the porous crystalline material. The conditions may be the same as, or different from, those used to steam the shell crystals 20 as described above. The steaming can be effected by heating the zeolite in the presence of steam at a temperature of at least about 900° C., preferably about 950 to about 1075° C., and most preferably about 1000 to about 1050° C., and for time period of from about 10 minutes to about 10 hours, preferably from 30 minutes to 5 hours, such as 30 minutes to 2 hours. Other preferred temperature and temperature ranges include any of the lower temperatures and/or times listed in this paragraph to any of the higher temperatures and/or times listed herein, e.g., from about 900 to 1050° C. for about 10 minutes to 2 hours, and so on.

The catalyst system employed in the present process preferably includes a binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials.

Naturally occurring clays which can be utilized in the present catalyst include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. It will be recognized that the specific clay used and treatment thereof will affect performance to some extent, and the determination of the most appropriate clay (or binder more generally) is within the skill of the ordinary artisan in possession of the present disclosure to determine by routine experimentation.

In addition to the foregoing materials, the core-shell catalyst can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

Generally, the catalyst composition will contain from 50 to 90 wt % of the binder.

Different synthesis methods can be applied for achieving the core-shell structure. One method is to grow the shell crystals on the core crystals. Another method is to begin the synthesis of the core crystals and add the proper reagents at a point during the synthesis to start crystallization of the shell crystals. A different approach is to deposit an amorphous silica alumina on the core crystal, followed by modification and crystallization of the amorphous silica into the desired shell crystal structure. A similar method synthesizes the core crystals with a binder into an extrudate that could be converted to the shell crystals. Yet another method involves conventional synthesis of the core crystals followed by vapor growth of the shell crystals. Other methods that may be used removes aluminum (by steaming or a chemical leaching method) from the core crystals to create a mesoporous defected surface that can then be used for the shell crystals to grow on, or impregnates the mesoporous shell of the core crystals with the shell crystals' structure directing agent and then crystalizes the shell crystals.

The alkylation process can be conducted in any known reaction vessel but generally the methanol and aromatic feeds are contacted with the catalyst described above with the catalyst particles being disposed in one or more fluidized beds. Each of the methanol and aromatic feeds can be injected into the fluidized catalyst in a single stage. However, in one embodiment, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed. Alternatively, the catalyst can be disposed in a plurality of vertically spaced catalyst beds, with the aromatic feed being injected into a lower portion of the first fluidized bed and part of the methanol being injected into an intermediate portion of the first bed and part of the methanol being injected into or between adjacent downstream catalyst beds.

One particular system for the alkylation process disclosed herein is described in U.S. Pat. No. 9,095,831. However, is the embodiments disclosed herein are generally applicable to fixed bed, moving bed, or fluid bed reactors.

The conditions employed in the alkylation stage of the present process are not narrowly constrained but, in the case of the methylation of toluene, generally include the following ranges: (a) temperature between about 400 and about 700° C., such as between about 450 and about 650° C.; (b) pressure of between about 1 atmosphere and about 1000 psig (between about 100 and about 7000 kPa), such as between about 10 psig and about 50 psig (between about 170 and about 1480 kPa); (c) moles toluene/moles methanol (in the reactor charge) of at least about 0.2, such as from about 0.2 to about 20; and (d) a weight hourly space velocity (WHSV) for total hydrocarbon feed to the reactor(s) of about 0.2 to about 1000, such as about 0.5 to about 500 for the aromatic reactant, and about 0.01 to about 100 for the combined methanol reagent stage flows, based on total catalyst in the reactor(s).

In addition to producing para-xylene and other xylene isomers, the present process produces water vapor which, at the high temperatures employed in the process, can lead to rapid aging of the catalyst. Notwithstanding that water is produced in the reaction, water is also advantageously and preferably added to the reaction, such as in one or more of the aromatic feed(s) and/or alkylating agent feed(s). Addition of water in this manner has been found to increase alkylation agent conversion, decrease side reactions, and also decrease coking in furnace(s) used to heat feedstreams to the reactor.

As is shown in the following Example, the present catalyst exhibits suppressed $C_1$-$C_5$ non-aromatics formation and an improved aromatics yield. Additionally, the use of a Group 6-14 metal increases methanol utilization by shifting the kinetic equilibrium of the reactions. This allows less reactants to be used to yield the same amount of para-xylene and smaller equipment downstream of the methylation reactor to process the $C_1$-$C_5$ non-aromatic by-products.

EXAMPLE

Figure 3:
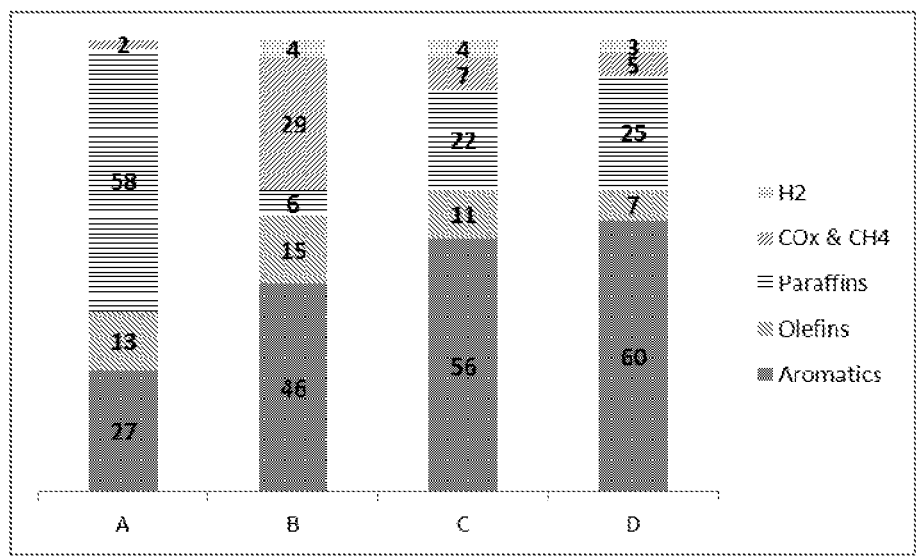
FIG. 3 is a comparative chart of the components in the product streams of Reactions A-D in the Example.

FIG. 3 shows the results from converting methanol to aromatics and olefins with three different catalysts at varying reaction conditions. In FIG. 3, the results are displayed as a bar graph for each reaction, with the weight percent of each reaction product designated by different shaded sections. Reaction A used a ZSM-5 catalyst at a temperature of 535° C., a methanol partial pressure of 15 psig, and a weight hourly space velocity (WHSV) of 2 hr$^{-1}$. Reaction B used a ZSM-5 catalyst with 1 wt % zinc dispersed thereon at a temperature of 500° C., a methanol partial pressure of 15 psig, and a weight hourly space velocity (WHSV) of 2 hr$^{-1}$. Reaction C used a ZSM-5 catalyst with 1 wt % zinc dispersed thereon at a temperature of 450° C., a methanol partial pressure of 15 psig, and a weight hourly space velocity (WHSV) of 2 hr$^{-1}$. Reaction D used a ZSM-5 catalyst with 1 wt % zinc and 1 wt % of phosphorus dispersed thereon at a temperature of 450° C., a methanol partial pressure of 15 psig, and a weight hourly space velocity (WHSV) of 2 hr$^{-1}$. All conversion reactions were performed to achieve 100% conversion of the methanol feed. While none of the catalysts used in Reactions A-D were core-shell catalysts, FIG. 3 shows that the addition of a Group 6-14 metal to the catalyst decreases the amount of olefins formed and increases the amount of aromatics produced.

While this disclosure includes description and illustrations that reference particular embodiments, those of ordinary skill in the art will appreciate that the embodiments disclosed herein lend themselves to variations not necessarily illustrated herein.

The invention claimed is:

1. A process for producing para-xylene, the process comprising:
   (a) providing a catalyst comprising core crystals of a first medium-pore size aluminosilicate zeolite having a pore size of about 5 to about 7 Angstroms and a discontinuous layer of shell crystals of a second medium-pore size aluminosilicate zeolite covering at least a portion of the external surface of the core crystals in a fluidized bed reactor, wherein the first medium-pore size aluminosilicate zeolite has a lower silica/alumina molar ratio than that of the second medium-pore size aluminosilicate zeolite;
   (b) alkylating $C_{6+}$ aromatic hydrocarbons with an alkylating agent selected from methanol, dimethyl ether, and mixtures thereof, on contacting the shell crystals under conditions including a temperature of at least 400° C. to produce a mixture comprising olefins and/or paraffins, para-xylene, unconverted alkylating agent, and unconverted C6+ aromatics hydrocarbons; and
   (c) converting the olefins and/or the paraffins formed in step (b), unconverted alkylating agent, and unconverted $C_{6+}$ aromatic hydrocarbons to para-xylene on contacting the core crystals.

2. The process of claim 1, wherein the second medium-pore size aluminosilicate zeolite comprises ZSM-5 having a silica/alumina molar ratio of at least 200, as measured prior to any steaming of the catalyst.

3. The process of claim 1,
   wherein the second medium-pore size aluminosilicate zeolite comprises ZSM-5 and phosphorus or a compound thereof;
   wherein (a) further comprises steaming the catalyst at a temperature of at least 900° C. so that the catalyst has a Diffusion Parameter for 2,2 dimethylbutane of about 0.1-15 sec$^{-1}$ when measured at a temperature of 120° C. and a 2,2 dimethylbutane pressure of 60 torr (8 kPa).

4. The process of claim 1, wherein the first medium-pore size aluminosilicate zeolite comprises ZSM-5 having a lower silica/alumina molar ratio than that of the second medium-pore size aluminosilicate zeolite.

5. The process of claim 1, wherein the first medium-pore size aluminosilicate zeolite comprises ZSM-5 having a silica/alumina molar ratio of about 10-100, as measured prior to any steaming of the catalyst, and about 0.01 to 2 wt % of at least one Group 6-14 element.

6. The process of claim 5, wherein the first medium-pore size aluminosilicate zeolite comprises from about 0.8-1.2 wt % of the Group 6-14 element.

7. The process of claim 5, wherein the Group 6-14 element is selected from the group consisting of Zn, Ga, Cu, Ag or Pt.

8. The process of claim 7, wherein the Group 6-14 element comprises Zn or Ga.

9. The process of claim 1, wherein the catalyst further comprises a binder.

10. The process of claim 9, wherein the binder comprises silica and/or clay.

11. The process of claim 9, wherein the catalyst contains from 75 to 90 wt % binder.

12. The process of claim 1, wherein the second medium-pore size aluminosilicate zeolite has been steamed at a temperature of at least 900° C. for between about 10 minutes and about 1.5 hours.

13. The process of claim 1, wherein said conditions in (b) also include a temperature between about 500 and 700° C., a total reactor pressure of between about 1 atmosphere and 1000 psig (100 and 7000 kPa), a weight hourly space velocity between about 0.5 and about 1000 and a molar ratio of toluene to methanol of at least about 0.2.

14. A process for producing para-xylene, the process comprising:
   (a) providing a core-shell catalyst comprising a discontinuous layer of shell crystals covering at least a portion of the external surface of core crystals in a fluidized bed reactor,
   wherein the shell crystals comprise ZSM-5 having a silica/alumina molar ratio of at least 200, as measured prior to any steaming of the catalyst, and phosphorus or a compound thereof, wherein the catalyst has been steamed at a temperature of at least 900° C., wherein said steamed catalyst has a Diffusion Parameter for 2,2 dimethylbutane of about 0.1-15 sec$^{-1}$ when measured at a temperature of 120° C. and a 2,2 dimethylbutane pressure of 60 torr (8 kPa),
   wherein the core crystals comprise ZSM-5, and the ZSM-5 of the core crystals has a lower silica/alumina molar ratio than that of the shell crystals;
   (b) alkylating $C_{6+}$ aromatic hydrocarbons with an alkylating agent selected from methanol, dimethyl ether, and mixtures thereof, on contacting the shell crystals to produce a mixture comprising olefins and/or paraffins, para-xylene, unconverted alkylating agent, and unconverted C6+ aromatics hydrocarbons; and
   (c) converting the olefins and/or the paraffins formed in step (b), unconverted alkylating agent, and unconverted $C_{6+}$ aromatic hydrocarbons to para-xylene on contacting the core crystals.

15. The process of claim 14, wherein the core crystals comprise ZSM-5 having a silica/alumina molar ratio of about 10-100, as measured prior to any steaming of the catalyst, and about 0.01 to 2 wt % of at least one Group 6-14 element.

16. The process of claim 14, wherein the core crystals comprise from about 0.8-1.2 wt % of the Group 6-14 element and wherein the Group 6-14 element is selected from the group consisting of Zn, Ga, Cu, Ag or Pt.

17. The process of claim 14, wherein the catalyst further comprises a binder.

18. The process of claim 14, wherein said conditions in (b) also include a temperature between about 500 and 700° C., a total reactor pressure of between about 1 atmosphere and 1000 psig (100 and 7000 kPa), a weight hourly space velocity between about 0.5 and about 1000 and a molar ratio of toluene to methanol of at least about 0.2.

* * * * *